US009622428B2

(12) United States Patent
Kerrigan et al.

(10) Patent No.: US 9,622,428 B2
(45) Date of Patent: Apr. 18, 2017

(54) HYBRID MUSHROOM STRAIN J11500 AND DESCENDANTS THEREOF

(71) Applicant: Sylvan America, Inc., Kittanning, PA (US)

(72) Inventors: Richard W. Kerrigan, Kittaning, PA (US); Mark P. Wach, Allison Park, PA (US); Michelle E. Schultz, New Bethlehem, PA (US)

(73) Assignee: Sylvan America, Inc., Kittanning, PA (US)

(*) Notice: Subject to any disclaimer, the term of this patent is extended or adjusted under 35 U.S.C. 154(b) by 490 days.

(21) Appl. No.: 14/169,658

(22) Filed: Jan. 31, 2014

(65) Prior Publication Data

US 2015/0216128 A1 Aug. 6, 2015

(51) Int. Cl.
*A01H 15/00* (2006.01)
*A01H 1/04* (2006.01)
*C12R 1/645* (2006.01)

(52) U.S. Cl.
CPC ............... *A01H 1/04* (2013.01); *C12R 1/645* (2013.01)

(58) Field of Classification Search
None
See application file for complete search history.

(56) References Cited

U.S. PATENT DOCUMENTS 9,017,988 B1 * 4/2015 Kerrigan ................. C12R 1/645 435/254.1

OTHER PUBLICATIONS

Hintz et al 1985 Current Genetics 9: 127-132.*
M. Imbernon et al., Mycologia, 88(5), 749-761 (1996).
Joint Genome Institute of California USA (Morin, et al., 2012).
R.W. Kerrigan, et al., in Genetics, 133, 225-236 (1993).
Velco, A.J. Jr, Kerrigan, R.W., MacDonald, L.A., Wach, M.P., Schlagnhaufer, C., and Romaine, C.P. 2004, Expression of novel genes in Agaricus bisporus using an Agrobacterium . . . .

* cited by examiner

*Primary Examiner* — David H Kruse
(74) *Attorney, Agent, or Firm* — Renner Kenner Greive Bobak Taylor & Weber

(57) ABSTRACT

A hybrid mushroom culture of *Agaricus bisporus*, designated as strain J11500, includes a representative culture of the strain, which has been deposited under NRRL Accession No. 50895. A method of producing a hybrid mushroom culture of *Agaricus bisporus* comprising: mating a homokaryotic line J10102-s69 with a homokaryotic line OWNC. Additionally, mushrooms, parts of the culture and products incorporating the culture are provided.

23 Claims, No Drawings

HYBRID MUSHROOM STRAIN J11500 AND DESCENDANTS THEREOF

TECHNICAL FIELD

This invention relates to a novel class of hybrid cultures of the edible, cultivated mushroom fungus *Agaricus bisporus* (Lange) Imbach, and methods of producing and using said hybrid culture. More particularly, this invention relates to a newly developed hybrid strain designated J11500 and to cultures that are descended, or otherwise derived, from *Agaricus bisporus* strain J11500.

BACKGROUND OF THE INVENTION

The edible mushroom *Agaricus bisporus* (Lange) Imbach var. *bisporus*, a microorganism belonging to the basidiomycete fungi, is widely cultivated around the world. In Europe and North America, it is the most widely cultivated mushroom species. The value of the annual *Agaricus bisporus* mushroom crop in the United States was about $1,110,000,000 in 2012-2013, according to the National Agricultural Statistics Service, Agricultural Statistics Board, U.S. Department of Agriculture (Aug. 20, 2013).

Cultures of *Agaricus*, like those of other microorganisms, are prepared, maintained, propagated and stored on sterile media using microbiological laboratory methods. Sterile tools and aseptic techniques are used within clean rooms or sterile transfer hoods to manipulate cells of the pure cultures for various purposes including clonal propagation and for the development of new strains using diverse techniques including spore germinations on sterile growth media and controlled matings on sterile growth media. Commercial culture inocula including mushroom 'spawn' and 'casing inoculum' are also prepared using large-scale microbiological production methods, for example by aseptically introducing inoculum of a pure culture of a strain of *Agaricus bisporus* into from one to 14,000 liters of sterilized growth media under sterile conditions, and are provided to the end user as pure cultures on sterile growth media contained within sterile packaging.

Mushrooms are cultivated commercially within purpose-built structures on dedicated farms. While there are many variations on methods, the following description is typical. Compost prepared from lignocellulosic material such as straw, augmented with nitrogenous material, is finished and pasteurized within a suitable facility. Mushroom spawn, which comprises a sterilized friable 'carrier substrate' onto which a pure culture of one mushroom strain has been aseptically incorporated via inoculum and then propagated, is mixed with the pasteurized compost and is incubated for approximately 13 to about 19 days at a controlled temperature, during which time the mycelium of the mushroom culture colonizes the entire mass of compost and begins to digest it. A non-nutritive 'casing layer' of material such as peat is then placed over the compost to a depth of from about 1.5 to about 2 inches. Additional 'casing inoculum' incorporating the same mushroom culture may be incorporated into the casing layer to accelerate the formation and harvesting of mushrooms, and improve uniformity of the distribution of mycelium and mushrooms in and on the casing surface. Environmental conditions, including temperature and humidity, in the cropping facility are then carefully managed to promote and control the transition of the culture from vegetative to reproductive growth at the casing/air interface. In a further about 13 to about 18 days after casing, mushrooms will have developed to the correct stage for harvest and sale. A flush of mushrooms comprising the original culture will be picked over a 3 to 4 day period. Additional flushes of mushrooms appear at about weekly intervals. Commercially, two or three flushes of mushrooms are produced and harvested before the compost is removed and replaced in the cropping facility.

Seventy to ninety-five percent of the *Agaricus* mushrooms cultivated in the United States, Europe, and elsewhere have a white pileus color, in accordance with consumer preferences. Market requirements for white mushrooms in the USA and elsewhere are narrow and precise for many observable phenotypic traits such as size, shape, color, color retention, firmness, and related traits such as shelf life. Consequently, genetically different strains of commercially successful white *Agaricus bisporus* mushrooms are not easily differentiated on the basis of appearance of the mushrooms, which must conform to the relatively strict market requirements. Strains may be differentiated on the basis of traits associated with the mushroom, such as mushroom size, mushroom shape (e.g., cap roundness, flesh thickness), color (i.e., white cap versus brown cap), surface texture (e.g., cap smoothness), tissue density and/or firmness, delayed maturation, basidial spore number greater than two, sporelessness, increased dry matter content, improved shelf life, and reduced bruising, as well as traits associated with the culture itself, and/or products incorporating the culture, and/or crops incorporating the culture, including increased crop yield, altered distribution of yield over time, decreased spawn to pick interval, resistance to infection by, symptoms of, or transmission of bacterial, viral or fungal diseases, insect resistance, nematode resistance, ease of crop management, suitability of crop for mechanical harvesting, and behavioral responses to environmental conditions including stressors, nutrient substrate composition, seasonal influences, farm practices, self/non-self interactions (compatibility or incompatibility) with various mushroom strains, to give some examples. Strains may also be differentiated based on their genotypic fingerprint (presence of specific alleles at defined marker loci in the nuclear or mitochondrial genome). Strains may have different ancestry, which will be reflected directly by the genotype, and indirectly, in some cases, by the phenotype.

Circa 1980, the first two white hybrid strains of *A. bisporus*, developed by a laboratory at Horst, the Netherlands, were introduced into commercial cultivation. These two "Horst" strains, called U1 and U3, are closely related hybrid strains produced by matings between two pre-existing white cultivated strains, as per M. Imbernon et al., *Mycologia,* 88(5), 749-761 (1996), herein incorporated by reference. The two parents of U1 and U3 are commercial strains belonging to two longstanding categorical types of strains known as the 'smooth-white' (SW) strains and the 'off-white' (OW) strains. The original homokaryons (or 'lines') obtained from the SW and OW strains, and used in the hybridization that produced the U1 strain, were designated H39 and H97 respectively; these cultures may no longer exist (A. Sonnenberg, pers. comm.). However, a number of laboratories have deheterokaryotized the U1 strain and obtained neohaplont cultures incorporating one or the other nuclear type corresponding to those contributed by H39 or H97, as well as the mitochondrial type of U1. We refer to these two types of neohaplonts of U1 categorically as the SWNC and OWNC lines or homokaryons, respectively. An OWNC line designated 'H97' was deposited in the public culture collection of the Fungal Genetics Stock Center of Kansas, USA, by A. Sonnenberg, under the number 10389, and in the public collection of the American Type Culture Collection of Maryland, USA, under the number MYA-4626. The genome of H97 was sequenced and placed in the public domain by the Joint Genome Institute of California, USA (Morin et al. 2012, herein incorporated by reference).

The U1 strain is thought to be the direct progenitor of all other white *A. bisporus* mushrooms currently cultivated in most regions of the world. Many commercial mushroom strains developed from U1 such as A15 and S130 meet the criteria for Essentially Derived Varieties (as the term is applied to plant varieties) of U1, having been developed from spores of the initial strain which retain the great majority of the parental genotype (this behavior was shown by R. W. Kerrigan et al. in *Genetics,* 133, 225-236 (1993), herein incorporated by reference). A group of strains developed either by cloning or by spore culture, or by any other method of 'essential derivation' as discussed below, from a single progenitor (as opposed to outbreeding between two different progenitors) is called a derived lineage group. Except for relatively minor acquired genetic differences all white strains developed within the Horst U1 derived lineage group share a single composite N+N heterokaryotic genotype, or a subset of that genotype, with the original U1 strain. For this reason, modern white *Agaricus* mushroom cultivation is effectively a monoculture.

*Agaricus bisporus* has a reproductive syndrome known as amphithallism, in which two distinct life cycles operate concurrently. As in other fungi, the reproductive propagule is a spore. *Agaricus* produces spores meiotically, on a meiosporangium known as a basidium. In a first life cycle, *A. bisporus* spores each receive a single haploid postmeiotic nucleus; these spores are competent to mate but not competent to reproduce mushrooms. These haploid spores germinate to produce homokaryotic offspring or lines which can mate with other compatible homokaryons to produce novel hybrid heterokaryons that are competent to produce mushrooms. Heterokaryons generally exhibit much less ability to mate than do homokaryons. This lifecycle is called heteromixis, or more commonly, outbreeding. This life cycle operates but typically does not predominate in strains of *Agaricus bisporus* var. *bisporus.*

A second, inbreeding life cycle called intramixis predominates in most strains of *Agaricus bisporus* var. *bisporus*. Most spores receive two post-meiotic nuclei, and most such pairs of nuclei consist of Non-Sister Nuclear Pairs (NSNPs) which have a heteroallelic genotype at most or all centromeric-linked loci including the MAT locus. That MAT genotype determines the heterokaryotic phenotype of these offspring, which are reproductively competent and can produce a crop of mushrooms. Unusually among eukaryotes, relatively little chromosomal crossing-over is observed to have occurred in postmeiotic offspring of *A. bisporus*; empirically, very little heteroallelism (analogous to heterozygosity) is lost among heterokaryotic offspring of a heterokaryotic strain. Consequently, parental and offspring heterokaryotic genotypes and phenotypes tend to closely resemble each other, as noted above; for this reason, essential derivation, e.g., the production of Essentially Derived Varieties (EDVs), is a familiar strain development technique among commercial mushroom spawn producers.

Strains currently available to the mushroom industry allow growers to produce crops of mushrooms successfully and profitably. Several factors exist that influence the degree of success and profitability achieved. Characteristics of strains that are factors which can improve producer profitability include increased productivity (higher yield or shorter cycle time), accelerated revenue capture (earlier harvest), reduced costs (for example, greater ease and speed of harvesting), reduced shrinkage (pre-sale weight loss), reduced overweighting of product in packages (extra weight of product packaged, due to particular sizes of individual mushrooms), improved consistency of crop performance responses to variations in raw materials, growing conditions and practices, superior crop performance in particular facilities, regions, etc., reduced losses to diseases including viral, bacterial and fungal disease agents, reduced losses to insect and nematode pests of the crop. There also exist improvable properties of the mushroom product that increase consumer and marketer demand in the distribution chain, and thus increase sales volume and/or sales price, such as improved visual appeal (more desirable coloration, shape, size, or surface texture), improved or distinct flavor characteristics, improved keeping qualities (longer persistence of desirable visual attributes), etc. Thus there are many characteristics by which a novel strain might be judged as superior in a particular production facility or sales market, or in the industry regionally or globally. Thus, the need continues to exist for new hybrid strains of *Agaricus bisporus* mushroom cultures and microorganisms that provide improved characteristics for producer profitability and for improved mushroom products over other previous strains of *Agaricus bisporus.*

There is also a need for commercially acceptable *A. bisporus* strains with different genotypes, relative to the U1 derived lineage group, for two reasons. First, strains incompatible with strains of the U1 derived lineage group are known to retard the spread of viral diseases between strains. Second, it is well understood that when an agricultural crop industry relies extensively on a single genetic lineage (i.e., creates a commercial monoculture as now exists for the white-capped U1 lineage of *A. bisporus*), there is an increased risk of unpredictable, catastrophic crop failure on a facility-wide or industry-wide scale. Therefore from a risk management and food security perspective, it is highly desirable to simultaneously provide both genetic diversification and commercially acceptable performance and crop characteristics.

SUMMARY OF THE INVENTION

The present invention is generally directed to a new and distinct *Agaricus bisporus* mushroom culture comprising the newly developed hybrid strain J11500 or Essentially Derived Varieties (EDVs) of strain J11500. A deposit of a culture of hybrid strain J11500, as disclosed herein, has been made with the Agricultural Research Services Culture Collection (NRRL) 1815 North University Street, Peoria, Ill. 61604 USA. The date of deposit was Jan. 15, 2014. The culture deposited was taken from the same culture maintained by Sylvan America, Inc., Kittanning, Pa., the assignee of record, since prior to the filing date of this application. All restrictions upon the deposit have been removed, and the deposit is intended to meet all deposit requirements of the U.S. Patent and Trademark Office, including 37 C.F.R. Sec. 1.801-1.809, and all deposit requirements under the Budapest Treaty. The NRRL Accession No. is 50895. The deposit will be maintained in the depository for a period of 30 years, or 5 years after the last request, or for the effective life of the patent, whichever is longer, and will be replaced as necessary during that period. The strain will be irrevocably and without restriction or condition released to the public upon the filing the priority application or upon the issuance of a patent on this strain according to the patent laws.

Such cultures of strain J11500 are noted to produce mushrooms, parts of mushrooms, parts of the culture, and strains and lines descended or derived from such cultures. Thus, the present invention encompasses strain J11500, Essentially Derived Varieties of strain J11500, dormant or active growing cultures present in dormant or germinating spores of strain J11500, and cultures incorporating the genetic material of strain J11500. The present invention is also directed towards methods of making and using strain J11500.

With respect to spores, living spores are heterokaryons or homokaryons in a dormant state. Spores are one part of the mushroom organism. Other parts include caps, stems, gills, cells (defined as hyphal compartments incorporating nuclei, mitochondria, cytoplasm, protoplasts, RNA, DNA, proteins, cell membranes, and cell walls including crosswalls), hyphae, and mycelium. Spores may be aseptically collected on sterile material, suspended in sterile water at various dilutions, and plated onto sterile agar growth media in order to produce germinated spores and the cultures incorporated within the spores. A preferred technique is to have within the enclosed petri plate a living *Agaricus* culture which may stimulate spore germination via the diffusion of a volatile pheromone. Germinated spores may be isolated under a microscope using sterile microtools such as steel needles, onto fresh nutrient agar plates. Using this method, heterokaryotic and homokaryotic offspring of strain J11500 comprising the spores and the cultures incorporated within the spores of strain J11500 may be obtained.

Development of novel hybrid varieties via heteromixis comprises the controlled physical association and mating of two compatible cultures to obtain a novel heterokaryon culture. Homokaryons (='lines') are the preferred starting cultures for making matings as they have maximal ability to anastomose and achieve plasmogamy with other cultures. Heterokaryons may also be placed in physical contact but with commercially unreasonably low probabilities of a mating resulting in successful formation of a novel heterokaryon. Compatibility is determined by the genotype at the MAT locus; two homokaryons with the same MAT allele cannot establish a heterokaryon after anastomosis. In a defined mating program, homokaryotic lines are obtained and are associated in predetermined pairwise combinations. In one method, homokaryon pairs may be placed in close proximity on the surface of a nutrient agar medium in a petri dish and allowed to grow together (in a physical association), at which point anastomoses between the two cultures occur. A successful outcome is a mating. The novel hybrid heterokaryon may be obtained by transferring mycelium from the fusion zone of the dish. Such a paired mating method was used to develop the strain J11500.

In contrast, EDVs are most often derived directly from a single initial culture (e.g., strain); all such derivations produce EDVs. There is no universally accepted definition of an EDV; one example of a definition applicable to plant varieties is provided by the US Plant Variety Protection Act (revised edition, February 2006). The definition employed herein is congruent with the term as it is widely understood. 'Essential derivation' methods of obtaining cultures which are by definition consequently EDVs of a single initial culture of *A. bisporus* include somatic selection, tissue culture selection, single spore germination, multiple spore germination, selfing, repeated mating back to the initial culture, mutagenesis, and transformation, to provide some examples. DNA-mediated transformation of *A. bisporus* has been reported by Velcko, A. J. Jr., Kerrigan, R. W., MacDonald, L. A., Wach, M. P., Schlagnhaufer, C., and Romaine, C. P. 2004, Expression of novel genes in *Agaricus bisporus* using an Agrobacterium-mediated transformation technique. Mush. Sci. 16: 591-597, and references therein, herein incorporated by reference. Transformation may introduce a single new gene or allele into the genome of an initial culture.

EDVs are unambiguously recognizable by their genotype, which will be predominantly a subset that of the single initial culture. Percentages of the initial genotype that will be present in *Agaricus bisporus* EDVs range from almost 100% in the case of somatic selections, to 99.x % in the case of strains modified by DNA-mediated transformation, to 90-99.x % in the case of single or multiple spore selections or some mutagenesis, to an average of 75-85% in the case of sibling-offspring matings (=selfing). Many methods of genotype determination, including methods described below, and others well known in the art, may be employed to determine the percentage of DNA of an initial culture that is present in another culture.

Repeated mating back to the initial culture to introgress a single trait into the genetic background of an initial culture is called introgressive trait conversion, and according to accepted definitions of EDVs, also produces an EDV of the initial culture. In a hypothetical example, in the first successive repetition of this process a resultant strain of this generation will have on average about 75% of the DNA of the initial strain while about 25% of the DNA will have been contributed by a second strain or line; as this process is repeated the DNA representation of the initial strain will increase, approaching 97% on average after 3 further successive repetitions. There is no universally accepted quantitative threshold for the proportion of DNA contributed by an initial culture in an EDV of an initial culture; we regard 75-100% genotype identity with an initial culture as indicative of an EDV of an initial culture. It is also established that an EDV of an EDV is also an EDV of an initial strain. Finally, because *Agaricus bisporus* alternates generations between heterokaryotic strains and homokaryotic lines, the criteria for essential derivation apply equally to cultures of both strains and lines.

Genotypic fingerprints are descriptions of the genotype at defined loci, where the presence of characterized alleles is recorded. Such fingerprints provide powerful and effective techniques for recognizing clones and all types of EDVs of an initial strain, as well as for recognizing ancestry within outbred lineages. Many techniques are available for defining and characterizing loci and alleles in the genotype. The most detailed approach is provided by whole-genome sequencing (WGS), which allows for direct characterization and comparison of DNA sequences across the entire genome. Using this approach to generate robust genotypic fingerprints incorporating large numbers of marker loci, it is possible to establish the nature of the relationship between two strains, including strains related by genealogical descent over several generations. Sylvan America, Inc., the inventor's assignee, has tracked genetic markers through four to six generations of its breeding pedigrees. If a sufficient number of rare markers are present in an initial strain or line, it will be possible to identify descent from an initial strain or line after several outbred generations without undue experimentation. In a hypothetical example, the mean expectation for genomic representation of an initial haploid line after 4 outbred generations is 3.1% ($50\%/2^4$) in an F4 hybrid, which corresponds to ca. 1 Mb of the nuclear genomic DNA of *A. bisporus*. Based on Sylvan America, Inc.'s analyses, that amount of DNA from each of two unrelated strains of *A. bisporus* may typically contain from about 10,000 to about 20,000 single nucleotide polymorphisms (SNPs), any one of which may provide a distinguishing marker linking the F4 hybrid to the initial line. By using multiple independent markers, ancestors of a strain can be identified with a very high probability of success and with reasonable confidence.

One trait of biological and commercial interest is heterokaryon incompatibility. The genetics of these self/non-self recognition systems are not well elucidated in basidiomycete fungi such as *Agaricus*, but are known in other genera to involve multiple alleles at multiple independent loci. Differences in the presumed genotype at the incompatibility loci prevent successful anastomoses and cytoplasmic continuity among physical mixtures of two or more heterokaryons. One consequence of such antagonistic responses is a retardation of growth and development, and a reduction of crop yield; this sort of partial crop failure is well known and evident to the experienced grower. Another consequence of heterokaryon incompatibility is restriction on the opportunity for endocellular viruses to move freely throughout or among mycelial networks. Virus diseases such as those caused by the LIV or MVX viruses can have severe negative impacts on facility productivity and must be remediated using hygiene practices which can be assisted by strain rotation. A method of improving mushroom farm hygiene called 'virus-breaking' is carried out by replacing cropping material (compost, spawn, casing inoculum) incorporating an initial strain with inoculum and cropping material incorporating another different strain that is incompatible with the initial strain. In the most effective implementation of the virus-breaking method, all biological material of the initial strain at a mushroom farm is replaced with biological material of the second, incompatible strain. Strain incompatibility creates an effective if not absolute barrier to movement of virus from biological reservoirs within a facility into new crops. Rotating cultivation usage among mushroom strains of different genotypes may also interrupt infection and infestation cycles of exogenous pests and pathogens.

As noted above, hybrid mushroom strain producers are always looking for hybrid strains that allow growers to produce crops of mushrooms successfully and profitably. In the case of strain J11500 and strains derived or descended from that strain, positive attributes documented thus far include a rounder cap shape and thicker cap flesh, both of which appeal to consumers, than existing successful commercial strain A-15, and a total harvested yield that may exceed that of strains like A-15, and yield timing that is accelerated as compared to strain A-15, a trait that is particularly suitable for certain segments of the market, and which tends to accelerate revenue capture and decrease crop cycle time (potentially allowing greater throughput).

In addition, strain J11500 has a different genotype from the U1 derived lineage group. Accordingly, strain J11500 is incompatible with strains of the U1 derived lineage group, which is a characteristic known to retard the spread of viral diseases between strains. Thus, strain J11500 confers a potential benefit in strain rotation programs designed to manage facility hygiene. Strain J11500 has been found to simultaneously provide both genetic diversification and commercially acceptable performance and crop characteristics.

These and other advantages of the present invention over existing prior art relating to *Agaricus bisporus* mushrooms and cultures, which shall become apparent from the description which follows, are accomplished by the invention as hereinafter described and claimed.

One or more aspects of the present invention may be accomplished by a hybrid mushroom culture of *Agaricus bisporus* designated as strain J11500, a representative culture of the strain having been deposited under NRRL Accession No. 50895. The strain J11500 may include various parts of the culture, including hyphae, spores, and cells and parts of cells, including, nuclei, mitochondria, cytoplasm, protoplasts, DNA, RNA, proteins, cell membranes and cell walls, said parts being present in at least one of the vegetative mycelium of the culture and mushrooms produced by the culture. The spores may be dormant or germinated spores, and may include heterokaryons and homokaryons incorporated therein.

One or more products incorporating the hybrid mushroom culture of *Agaricus bisporus* designated as strain J11500 may be produced. Such products include mycelium, spawn, inoculum, casing inoculum, fresh mushrooms, processed mushrooms, mushroom extracts and fractions, mushroom pieces, and colonized substrates selected from grain, compost, and friable particulate matter. It will be appreciated that mushroom pieces refer to stems, pilei, and other larger portions of the mushroom itself. Spores of the mushrooms may be dormant spores or germinated spores, and may include heterokaryons and homokaryons incorporated therein.

One or more other aspects of the present invention may be accomplished by an Essentially Derived Variety of the hybrid mushroom culture of strain J11500. In one or more embodiments, an *Agaricus bisporus* culture produced by essential derivation has at least one of the essential characteristics of strain J11500, for example the same heterokaryon compatibility phenotype, and/or the further characteristics of cap roundness, flesh thickness, yield performance, and yield timing relative to commercial strain A-15, wherein a culture of strain J11500 has been deposited under the NRRL Accession Number 50895.

Other aspects of the present invention may be accomplished by an *Agaricus bisporus* culture having the same physiological and morphological characteristics as strain J11500, wherein a culture of strain J11500 has been deposited under the NRRL Accession Number 50895. It will be appreciated that the physiological characteristics of the strain will include its performance characteristics as well.

Still further aspects of the present invention may be accomplished by a hybrid mushroom culture of *Agaricus bisporus* having a genotypic fingerprint which has characters at marker loci ITS, p1n150-G3-2, MFPC-1-ELF, AN, AF, and FF, wherein all of the characters of said fingerprint are present in the genotypic fingerprint of strain J11500. In one or more embodiments, the culture has a genotypic fingerprint having characters at marker loci described in Table VII, wherein all of the characters of said fingerprint are present in the genotypic fingerprint of strain J11500.

Other aspects of the invention may be achieved by a method for producing a hybrid mushroom culture of *Agaricus bisporus* that includes the step of mating a homokaryotic line J10102-s69, a culture of which was deposited under NRRL Accession No. 50893, with a homokaryotic line OWNC, a culture of which was deposited under NRRL Accession No. 50894. Such a mating provides the hybrid mushroom culture J11500, which exhibits antagonism toward heterokaryon strains in the U1 derived lineage group. The observable heterokaryon incompatibility demonstrates the genetic distinctness of strain J11500 relative to strains like A-15 that belong to the U1 derived lineage group. In one or more embodiments, the method further includes providing a mushroom culture of the invention in mushroom products selected from the group consisting of mycelium, spawn, inoculum, casing inoculum, fresh mushrooms, processed mushrooms, parts of mushrooms, mushroom extracts and fractions, mushroom pieces, and colonized substrates selected from grain, compost, and friable particulate matter. In other embodiments, the method may include providing the mushroom culture in derived cultures selected from the group consisting of homokaryons, heterokaryons, aneuploids, somatic subcultures, tissue explants cultures, protoplasts, dormant spores, germinating spores, inbred descendents and outbred descendents, transgenic cultures, and cultures having a genome incorporating a single locus conversion.

One or more further aspects of the present invention may be accomplished by a culture, a cell or a culture including the cell, produced by the method(s) above. Thus, one or more embodiments may include a method further including the step of growing the hybrid mushroom culture to produce hybrid mushrooms and parts of mushrooms. Other embodiments may provide for methods wherein the hybrid mushroom culture produced, or the cell, includes a marker profile having characters at marker loci ITS, p1n150-G3-2, MFPC-1-ELF, AN, AF, and FF, wherein all of the characters of said marker profile are also present in the marker profile of J11500. Still other embodiments may provide for methods wherein the hybrid mushroom culture produced, or the cell, includes a marker profile having characters at marker loci described in Table VII, wherein all of the characters of said marker profile are also present in the marker profile of J11500

Finally, another aspect of the present invention may be accomplished by a method that uses the hybrid mushroom culture selected from a strain J11500 or Essentially Derived Varieties of strain J11500, a representative culture of the strain having been deposited under NRRL Accession No. 50895. In one embodiment, the method further includes growing a crop of edible mushrooms by carrying out the steps described hereinabove. In another embodiment, the method may include using strain J11500 or essentially derived varieties of strain J11500 in crop rotation to reduce pathogen pressure and pathogen reservoirs in mushroom growing facilities as described hereinabove. In yet another embodiment, the method includes using strain J11500 and Essentially Derived Varieties of strain J11500 to produce offspring as described hereinabove.

DETAILED DESCRIPTION OF THE INVENTION

Initially, in order to provide clear and consistent understanding of the specification and claims, including the scope to be given such terms, the following definitions are provided.

Allele: A heritable unit of the genome at a defined locus, ultimately identified by its DNA sequence (or by other means).

Amphithallism: A reproductive syndrome in which heteromixis and intramixis are both active.

Anastomosis: Fusion of two or more hyphae that achieves cytoplasmic continuity.

Basidiomycete: A monophyletic group of fungi producing meiospores on basidia; a member of a corresponding subdivision of Fungi such as the Basidiomycetales or Basidiomycotina.

Basidium: The meiosporangial cell, in which karyogamy and meiosis occur, and upon which the basidiospores are formed.

Bioefficiency: For mushroom crops, the net fresh weight of the harvested crop divided by the dry weight of the compost substrate at the time of spawning, for any given sampled crop area or compost weight.

Breeding: Development of strains, lines or varieties using methods that emphasize sexual mating.

Cap: Pileus; part of the mushroom, the gill-bearing structure.

Cap Roundness: Strictly, a ratio of the maximum distance between the uppermost and lowermost parts of the cap, divided by the maximum distance across the cap, measured on a longitudinally bisected mushroom; typically averaged over many specimens; subjectively, a 'rounded' property of the shape of the cap.

Carrier substrate: A medium having both nutritional and physical properties suitable for achieving both growth and dispersal of a culture.

Casing layer, casing: A layer of non-nutritive material such as peat or soil that is applied to the upper surface of a mass of colonized compost in order to permit development of the mushroom crop.

Casing inoculum (CI): A formulation of inoculum material incorporating a mushroom culture, typically of a defined heterokaryotic strain, suitable for mixing into the casing layer.

Cloning: Somatic propagation without selection.

Combining ability: The capacity of an individual to transmit traits or superior performance to its offspring (known and available methods of assessment vary by trait).

Compatibility: See heterokaryon compatibility.

Culture: The tangible living organism; the organism propagated on various growth media and substrates; one instance of one physical strain, line, homokaryon or heterokaryon; the sum of all of the parts of the culture, including hyphae, mushrooms, spores, cells, nuclei, mitochondria, cytoplasm, protoplasts, DNA, RNA, proteins, cell membranes and cell walls.

Derivation: Development from a strain; see Essentially Derived Variety (EDV).

Derived lineage group: The set of EDVs derived from a single initial strain or variety.

Descent: Genealogical descent over a limited number (e.g., 10 or fewer) of generations.

Diploid: Having two haploid chromosomal complements within a single nuclear envelope.

Essential derivation: A process by which an Essentially Derived Variety is obtained from an initial variety or strain or from an EDV of an initial variety or strain; modification of an initial culture using methods including somatic selection, tissue culture selection, selfing including intramictic reproduction via single spores and multiple spores and mating of sibling offspring lines, back-mating to the initial variety, or mutagenesis and/or genetic transformation of the initial variety to produce a distinct culture in which the genotype of the resulting culture is predominantly that of the initial culture.

Essentially Derived Variety (EDV): (Note: EDV definitions incorporate elements of (1) relatedness, (2) methods of derivation, (3) and empirical tests.) In general, a variety that is predominantly derived from an initial variety or from an EDV of an initial variety, and which conforms to essential characteristics of the initial variety except for distinguishing differences resulting from the act of derivation, is an EDV of the initial variety. In the art of mushroom strain development, a strain or culture predominantly or entirely derived from a single initial strain or culture, thus having most or all, but at least 75%, of its genome or genotype present in the genome or genotype of the initial strain or culture; a strain or culture obtained from an initial strain or culture by somatic selection, tissue culture selection, selfing including mating of sibling offspring lines and intramictic reproduction via single or multiple spores, back-mating to the initial strain or culture, or mutagenesis and/or genetic transformation of the initial strain or culture; a strain or culture reconstituted from neohaplonts derived from an initial strain or culture, whether or not the haploid lines have been passed into or out of other heterokaryons; a strain or culture with the same essential phenotype as that of an initial strain or culture.

Flesh Thickness: A ratio of the maximum distance between the top of the stem and the uppermost part of the cap, divided by the maximum distance across the cap, measured on a longitudinally bisected mushroom; typically averaged over many specimens; subjectively called 'meatiness'.

Flush: A period of mushroom production within a cropping cycle, separated by intervals of non-production; the term flush encompasses the terms 'break' and 'wave' and can be read as either of those terms.

Fungus: An organism classified as a member of the Kingdom Fungi.

Genotypic fingerprint: A description of the genotype at a defined set of marker loci; the known genotype.

Gill: Lamella; part of the mushroom, the hymenophore- and basidium-bearing structure.

Haploid: Having only a single complement of nuclear chromosomes; see homokaryon.

Heteroallelic: Having two different alleles at a locus; analogous to heterozygous.

Heteroallelism: Differences between homologous chromosomes in a heterokaryotic genotype; analogous to heterozygosity.

Heterokaryon: As a term of art this refers to a sexual heterokaryon: a culture which has two complementary (i.e., necessarily heteroallelic at the Mat locus) types of haploid nuclei in a common cytoplasm, and is thus functionally and physiologically analogous to a diploid individual (but cytogenetically represented as N+N rather than 2N), and which is potentially reproductively competent, and which exhibits self/non-self incompatibility reactions with other heterokaryons; also called a strain or stock in the breeding context.

Heterokaryon compatibility: The absence of antagonism observed during physical proximity or contact between two heterokaryons that are not genetically identical; see Heterokaryon Incompatibility.

Heterokaryon incompatibility: The phenomenon of antagonism observed during physical proximity or contact between two heterokaryons that are not genetically identical; a multilocus self/non-self recognition system that operates in basidiomycete heterokaryons.

Heterokaryotic: Having the character of a heterokaryon.

Heteromixis: Life cycle involving mating between two different non-sibling haploid individuals or gametes; outbreeding.

Homoallelic: Having not more than one allele at a locus. The equivalent term in a diploid organism is 'homozygous'. Haploid lines are by definition entirely homoallelic at all non-duplicated loci.

Homokaryon: A haploid culture with a single type (or somatic lineage) of haploid nucleus (cytogenetically represented as N), and which is ordinarily reproductively incompetent, and which does not exhibit typical self/non-self incompatibility reactions with heterokaryons, and which may function as a gamete in sexually complementary anastomoses; a 'line' which, as with an inbred plant line, transmits a uniform genotype to offspring; a predominantly homoallelic line that mates well and fruits poorly is a putative homokaryon for strain development purposes; see discussion below.

Homokaryotic: Having the character of a homokaryon; haploid.

Hybrid: Of biparental origin, usually applied to heterokaryotic strains and cultures produced in controlled matings.

Hybridizing: Physical association, for example on a petri dish containing a sterile agar-based nutrient medium, of two cultures, usually homokaryons, in an attempt to achieve anastomosis, plasmogamy, and formation of a sexual heterokaryon (=mating); succeeding in the foregoing.

Hyphae: Threadlike elements of mycelium, composed of cell-like compartments.

Inbreeding: Matings that include sibling-line matings, back-matings to parent lines or strains, and intramixis; reproduction involving parents that are genetically related.

Incompatibility: See heterokaryon incompatibility.

Inoculum: A culture in a form that permits transmission and propagation of the culture, for example onto new media; specialized commercial types of inoculum include spawn and CI.

Intramixis: A uniparental sexual life cycle involving formation of a complementary 'mated' pair of postmeiotic nuclei within the basidium or individual spore.

Introgressive trait conversion: mating offspring of a hybrid to a parent line or strain such that a desired trait from one strain is introduced into a predominating genetic background of the other parent line or strain.

Lamella: see 'gill'.

Line: A culture used in matings to produce a hybrid strain; ordinarily a homokaryon which is thus homoallelic, otherwise a non-heterokaryotic (non-NSNPP) culture which is highly homoallelic; practically, a functionally homokaryotic and entirely or predominantly homoallelic culture; analogous in plant breeding to an inbred line which is predominantly or entirely homozygous.

Lineage group: see 'derived lineage group'. The set of EDVs derived from a single initial strain or variety.

Locus: A defined contiguous part of the genome, homologous although often varying among different genotypes; plural: loci.

Marker assisted selection: Using linked genetic markers including molecular markers to track trait-determining loci of interest among offspring and through pedigrees.

MAT: The mating-type locus, which determines sexual compatibility and the heterokaryotic state.

Mating: The sexual union of two cultures via anastomosis and plasmogamy; methods of obtaining matings between mushroom cultures are well known in the art.

Mycelium: The vegetative body or thallus of the mushroom organism, comprised of threadlike hyphae.

Mushroom: The reproductive structure of an agaric fungus; an agaric; a cultivated food product of the same name.

Neohaplont: A haploid culture or line obtained by physically deheterokaryotizing (reducing to haploid components) a heterokaryon; a somatically obtained homokaryon.

Offspring: Descendents, for example of a parent heterokaryon, within a single generation; most often used to describe cultures obtained from spores from a mushroom of a strain.

Outbreeding: Mating among unrelated or distantly related individuals.

Parent: An immediate progenitor of an individual; a parent strain is a heterokaryon, a parent line is a homokaryon; a heterokaryon may be the parent of an F1 heterokaryon via an intermediate parent line.

Pedigree-assisted breeding: The use of genealogical information to identify desirable combinations of lines in controlled mating programs.

Phenotype: Observable characteristics of a strain or line as expressed and manifested in an environment.

Plasmogamy: Establishment, via anastomosis, of cytoplasmic continuity leading to the formation of a sexual heterokaryon.

Progenitor: Ancestor, including parent (the direct progenitor).

Selfing: Mating among sibling lines; also intramixis.

Somatic: Of the vegetative mycelium.

Spawn: A mushroom culture, typically a pure culture of a heterokaryon, typically on a sterile substrate which is friable and dispersible particulate matter, in some instances cereal grain; commercial inoculum for compost; reference to spawn includes reference to the culture on a substrate.

Spore: Part of the mushroom, the reproductive propagule.

Stem: Stipe; part of the mushroom, the cap-supporting structure.

Sterile Growth Media: Nutrient media, sterilized by autoclaving or other methods, that support the growth of the organism; examples include agar-based solid nutrient media such as Potato Dextrose Agar (PDA), nutrient broth, and many other materials.

Stipe: see ‘stem’.

Strain: A heterokaryon with defined characteristics or a specific identity or ancestry; equivalent to a variety.

Tissue culture: A de-differentiated vegetative mycelium obtained from a differentiated tissue of the mushroom.

Trait conversion: Selective introduction of the genetic determinants of one (a single-locus conversion) or more desirable traits into the genetic background of an initial strain while retaining most of the genetic background of the initial strain. See ‘Introgressive trait conversion’ and ‘Transformation’.

Transformation: A process by which the genetic material carried by an individual cell is altered by the incorporation of foreign (exogenous) DNA into its genome; a method of obtaining a trait conversion including a single-locus conversion.

Virus-breaking: Using multiple incompatible strains, i.e. strains exhibiting heterokaryon incompatibility, successively in a program of planned strain rotation within a mushroom production facility to reduce the transmission of virus from on-site virus reservoirs into newly planted crops.

Yield: The net fresh weight of the harvest crop, normally expressed in pounds per square foot.

Yield pattern: The distribution of yield within each flush and among all flushes; influences size, quality, picking costs, and relative disease pressure on the crop and product.

With respect to the definition of homokaryon above, it is noted that homokaryons and homoallelic lines are subject to technical and practical considerations: A homokaryon in classical terms is a haploid culture which is axiomatically entirely homoallelic. In practical terms, for fungal strain development purposes, the definition is broadened somewhat to accommodate both technical limitations and cytological variation, by treating all predominately homoallelic lines as homokaryons. Technical limitations include the fact that genomes contain duplicated DNA regions including repeated elements such as transposons, and may also include large duplications of chromosomal segments due to historical translocation events; such regions may appear not to be homoallelic by most genotyping methods. Two different *A. bisporus* genomes sequenced by the Joint Genome Institute, a U.S. federal facility, differ in estimated length by 4.4%, and in gene numbers by 8.2%, suggesting a considerable amount of DNA duplication or rearrangement within different strains of the species. No presently available genome of *A. bisporus* can completely account for the physical arrangement of such elements and translocations, and so the assembled genome sequences of haploid lines may have regions that appear to be heteroallelic using currently available genotyping methods. Cytologically, a homokaryotic offspring will ordinarily be a spore that receives one haploid, postmeiotic nucleus. However, a spore receiving two third-division nuclei from the basidium will be genetically equivalent to a homokaryon. A spore receiving two second-division ‘sister’ postmeiotic nuclei will be a functional homokaryon even though some distal ‘islands’ of heteroallelism may be present due to crossovers during meiosis. Also, a meiosis that has an asymmetrical separation of homologues can produce an aneuploid, functionally homokaryotic spore in which an extra chromosome, producing a region of heteroallelism, is present. All of these cultures are highly homoallelic and all function as homokaryons. Technological limitations make it impractical to distinguish among such cultures, and also to rule out DNA segment duplication as an explanation for limited, isolated regions of the genome sequence assembly that appear to be heteroallelic. Therefore, in the present application, the use of the term ‘homoallelic’ to characterize a line includes entirely or predominately homoallelic lines, and cultures described in this way are functional homokaryons, are putatively homokaryotic, and are all defined as homokaryons in the present application.

Now, with respect to the invention and as noted hereinabove, the present invention relates to cultures of the hybrid *Agaricus bisporus* strain J11500 and to cultures derived or descended from J11500. Such cultures are used to produce mushrooms and parts of mushrooms. Thus, the present invention further relates to methods of making and using the strain J11500 and Essentially Derived Varieties (EDVs) of the strain J11500.

Hybrid strain J11500 is the product of 6 generations of controlled line matings by Sylvan America, Inc. The original mating was made between line JB 137-s8 and line SWNC. In the sixth generation, line J10102-s69, a descendent of the first hybrid (and of other hybrids produced by Sylvan, Inc.), was mated with line OWNC to produce the novel hybrid strain J11500.

Cultures of strain J11500 produce commercially acceptable and desirable crops of white mushrooms. Table I presents yield data as pounds per square foot, in three independent crop tests with internal replication. As shown in Table I, productivity of J11500 is comparable to and often greater than the productivity of the A15 strain, with total (3-flush) yield averaging 101.3% of the A-15 control and ranging as high as 106.8% under standard growing conditions for A-15. Distribution of the crop over the three-flush harvest period is relatively accelerated, meaning that more of the crop is picked during first flush, when disease pressure is lowest and product quality may be correspondingly higher. In a general t-test on this small data set, first break yield differences between J11500 and A-15 approached statistical significance (p=0.057).

TABLE I

| | 1st flush yield | | 1st & 2nd flush yield | | Total yield | |
|---|---|---|---|---|---|---|
| Test ID | J11500 | A-15 | J11500 | A-15 | J11500 | A-15 |
| 12-108 | 2.87 | 2.27 | 4.50 | 4.04 | 5.02 | 4.70 |
| 12-119 | 2.47 | 2.15 | 3.73 | 3.81 | 4.34 | 4.61 |
| 12-146 | 2.57 | 2.39 | 3.92 | 3.71 | 4.60 | 4.47 |
| Averages | 2.63 | 2.27 | 4.05 | 3.85 | 4.65 | 4.59 |
| % gain | +16% | | +5% | | +1% | |

Within first flush, yield is also accelerated. Over the four productive days of first flush, the cumulative daily yield data in Table II, reporting averages of the same three tests, shows that the harvest of strain J11500 is accelerated over that of the A-15 control.

TABLE II

| | Day (after casing): | | | |
|---|---|---|---|---|
| Cumulative daily yield: | 14 | 15 | 16 | 17 |
| J11500 yield as a percent of A-15 yield | 181% | 139% | 128% | 116% |

Timing to harvest is about equivalent to that of commercial strain A15 (both about 13 to 19 days), and sometimes may be slightly faster, which can be economically advantageous. Table III shows that in the same crop tests, on average, strain J11500 began to produce its crop 0.43 days before A-15, and the peak of production in the first flush was 0.24 days earlier for strain J11500.

TABLE III

| | Days to first pick | | Peak first flush pick day | |
|---|---|---|---|---|
| Test ID | J11500 | A-15 | J11500 | A-15 |
| 12-108 | 14.0 | 15.3 | 14.7 | 15.3 |
| 12-119 | 14.0 | 14.0 | 14.0 | 14.3 |
| 12-146 | 14.0 | 14.0 | 15.0 | 14.8 |
| Averages | 14.0 | 14.43 | 14.56 | 14.8 |
| Days gained | +0.43 | | +0.24 | |

Cap roundness and relative flesh thickness (i.e., 'meatiness') are considered to be desirable commercial mushroom traits. J11500 typically produces mushrooms with caps having thicker flesh, and which are subjectively rounder, than those of A15; objectively, the following physical measurement ratios demonstrate the shape differences of J11500 compared to A15.

Cap roundness, expressed as cap height/cap diameter (CH/CD) is an economically important trait reflecting a consumer preference for rounder mushrooms. Measurements were made on samples of 10 first break mushrooms of equivalent maturity from both J11500 and the commercial control A-15. J11500 was rounder (0.68) compared to the control A-15 (0.60), and this difference was significant (t-test, p=9.15E-07).

Similarly, cap 'meatiness', expressed as flesh thickness/cap diameter (FT/CD) is an economically important trait reflecting a consumer preference for thicker-fleshed mushrooms. Measurements were made on samples of 10 first break mushrooms of equivalent maturity from both J11500 and the commercial control A-15. J11500 was meatier (0.36) compared to the control A-15 (0.33), and this difference was significant (t-test, p=0.0054).

Cross-strainincompatibility can also be a useful commercial mushroom trait. J11500 is incompatible with A-15, a proxy for the U1 derived lineage group. When casing material incorporating inoculum of J11500 is placed over compost colonized with A-15, or conversely when A-15 is placed over J11500, a partial crop failure ensues, demonstrating incompatibility as shown by the yield data in TABLE IV:

TABLE IV

| Spawn strain | Casing strain | Identity | First flush yield |
|---|---|---|---|
| J11500 | J11500 | Self | 2.47 lbs. |
| A-15 | A-15 | Self | 2.03 lbs. |
| J11500 | A-15 | Non-self | 0.50 lbs. |
| A-15 | J11500 | Non-self | 0.17 lbs. |

The incompatibility of J11500 with A-15 is transmitted into spores and thus is inherited by EDVs derived from spores, as shown by the yield data in TABLE V:

TABLE V

| Spawn strain | Casing strain | Identity | First flush yield |
|---|---|---|---|
| A-15 | A-15 | Self | 1.74 lbs. |
| A-15 | J11500-ms2 | Non-self | 0.58 lbs. |
| A-15 | J11500-ms3 | Non-self | 0.63 lbs. |
| A-15 | J11500-ms4 | Non-self | 0.58 lbs. |
| A-15 | J11500-ms5 | Non-self | 0.44 lbs. |
| A-15 | J11500-ms10 | Non-self | 0.53 lbs. |

A test of compatibility of an EDV of strain J11500 (designated J11500-ms2) with the strain J11500 itself was performed and the results are shown in TABLE VI.

TABLE VI

| Spawn strain | Casing strain | Identity | First flush yield |
|---|---|---|---|
| J11500 | J11500 | Self | 1.95 lbs. |
| J11500 | J11500-ms2 | Self: EDV | 2.69 lbs. |
| J11500 | J11500-ms2 | Self: EDV | 3.13 lbs. |

Table VI shows that in test 13-177, the EDV strain designated J11500-ms2 was completely compatible with the initial strain J11500, and in fact demonstrated higher first break yield than strain J11500 as opposed to a partial crop failure that would have indicated incompatibility.

Given that strain J11500 has 4 non-cultivar progenitors and that considerable genetic diversity exists among strains, the genotypic fingerprint of strain J11500 shows numerous differences with that of the U1 lineage group. A unique fingerprint allows strain J11500 (and its Essentially Derived Varieties and descendents) to be unambiguously identified. Agronomically, genetic diversity among cultivated strains is a desirable objective because it is well established that genetic monocultures among agricultural crop species can lead to disastrous failures due to particular disease, pest, or environmental pressures. Any otherwise desirable commercial strain with genetic novelty is therefore valuable. Strain J11500 meets those criteria.

For the purpose of this invention, the whole genomic sequence of strain J11500 and of the cultures of its parent lines and of selected EDVs of J11500 have been obtained by Sylvan America Inc. using the following method. The homokaryotic parent line cultures were grown in sterile broth growth medium after maceration. After 2-4 weeks, hyphal cells were collected by filtration, were frozen at −80 C, and were lyophilized until dry. Cap tissue was obtained from mushrooms produced by cultures of the heterokaryotic J11500 (and EDV) strains, and was frozen and lyophilized. DNA was extracted using a CTAB protocol followed by RNAse treatment and gel purification. A contractor, SeqWright, prepared DNA libraries from the DNA of each culture, and sequenced the libraries using Illumina MiSeq technology. Assemblies of the reads into genomic sequence using the public-domain reference genome sequence of H97 was performed by the contractor. Consequently about 93% to about 95% of the entire genotype of strain J11500 and of three EDVs of strain J11500 are known to Sylvan America, Inc with certainty. The total number of markers distinguishing strain J11500 that are known to the assignee is about 300,000. A brief excerpt of the genotype strain J11500 at numerous sequence-characterized marker loci distributed at intervals along each of the 19 H97 V2.0 reference scaffolds larger than 100 Kb in length is provided in Table VII.

TABLE VII

| Scaffold | Position of SNA [H97 V2.0 ref. coords.] | Culture: J10102-s69 | OWNC | J11500 | J11500-ms2 |
|---|---|---|---|---|---|
| 1 | 99995 | CTAC***G***TTGA | CTACATTGA | CTAC***r***TTGA | CTAC***r***TTGA |
| 1 | 349966 | AAGG***C***GGTT | AAGGTGGTT | AAGG***y***GGTT | AAGG***y***GGTT |
| 1 | 600059 | TTTT***C***TTT***A*** | TTTTTTTT-C | TTTT***y***TT[-/A] | TTTT***y***TT[-/A] |
| 1 | 850014 | C***T***TTTTC***G***C | CCTTTTCAC | C***y***TTTTC***r***C | C***y***TTTTC***r***C |
| 1 | 1099971 | GTCG***G***CACC | GTCGACACC | GTCG***r***CACC | GTCG***r***CACC |
| 1 | 1350278 | GGAG***GT***TCG | GGAGAGTCG | GGAG***rk***TCG | GGAG***rk***TCG |
| 1 | 1599956 | AATA***G***GCGC | AATAAGCGC | AATA***r***GCGC | AATA***r***GCGC |
| 1 | 1850032 | CGAG***C***AATT | CGAGTAATT | CGAG***y***AATT | CGAG***y***AATT |
| 1 | 2119049 | ACAA***CT***CAA | ACAATCCAA | ACAA***yy***CAA | ACAA***yy***CAA |
| 1 | 2400243 | ACTT***G***ATGA | ACTTCATGA | ACTT***s***ATGA | ACTT***s***ATGA |
| 1 | 2612870 | AATA***A***GAGT | AATAGGAGT | AATA***r***GAGT | AATA***r***GAGT |
| 1 | 2858975 | GCCG***C***TCTT | GCCGTTCTT | GCCG***y***TCTT | GCCG***y***TCTT |
| 1 | 2804522 | GAAG***GG***GAC | GAAGACGAC | GAAG***rs***GAC | GAAG***rs***GAC |
| 1 | 3047987 | AAGG***A***GGGG | AAGGGGGGG | AAGG***r***GGGG | AAGG***r***GGGG |
| 1 | 3164166 | ATAA***TC***GGG | ATAAGGGGG | ATAA***ks***GGG | ATAA***ks***GGG |
| 1 | 3256057 | TATC***C***GTTT | TATCTGTTT | TATC***y***GTTT | TATC***y***GTTT |
| 2 | 101820 | ATTA***CG***GAT | ATTAAAGAT | ATTA***mr***GAT | ATTA***mr***GAT |
| 2 | 350156 | TCGG***A***GGTG | TCGGGGGTG | TCGG***r***GGTG | TCGG***r***GGTG |
| 2 | 600112 | ATGT***G***TACG | ATGTATACG | ATGT***r***TACG | ATGT***r***TACG |
| 2 | 850338 | TGGT***T***CTAA | TGGTGCTAA | TGGT***k***CTAA | TGGT***k***CTAA |
| 2 | 1099413 | CCTG***G***CTCA | CCTGACTCA | CCTG***r***CTCA | CCTG***r***CTCA |
| 2 | 1349512 | CTCA***A***CAGT | CTCAGCAGT | CTCA***r***CAGT | CTCA***r***CAGT |
| 2 | 1600085 | CACA***T***TGCC | CACAATGCC | CACA***w***TGCC | CACA***w***TGCC |
| 2 | 1901773 | ACTC***A***AATT | ACTCGAATT | ACTC***r***AATT | ACTC***r***AATT |
| 2 | 2150201 | GTCG***A***AGGT | GTCGTAGGT | GTCG***w***AGGT | GTCG***w***AGGT |
| 2 | 2400281 | TCAA***C***AC***T***C | TCAAAACCC | TCAA***m***AC***y***C | TCAA***m***AC***y***C |
| 2 | 2650136 | ATAA***A***TCCT | ATAATTCCT | ATAA***w***TCCT | ATAA***w***TCCT |
| 2 | 2903593 | ACTA***T***A***G***GA | ACTAAAAGA | ACTA***w***A***r***GA | ACTA***w***A***r***GA |
| 2 | 3048019 | GTCC***A***CTGC | GTCCGCTGC | GTCC***r***CTGC | GTCC***r***CTGC |
| 3 | 65650 | GGCG***G***TTTT | GGCGCTTTT | GGCG***s***TTTT | GGCG***s***TTTT |
| 3 | 119281 | TTTA***C***ACTC | TTTATACTC | TTTA***y***ACTC | TTTA***y***ACTC |
| 3 | 249570 | GTAT***T***ATGT | GTAT***T***ATGT | GTAT***T***ATGT | GTAT***T***ATGT |
| 3 | 750000 | GTCC***G***GCCA | GTCC***G***GCCA | GTCC***G***GCCA | GTCC***G***GCCA |

TABLE VII-continued

| Scaffold | Position of SNA [H97 V2.0 ref. coords.] | Culture: J10102-s69 | OWNC | J11500 | J11500-ms2 |
|---|---|---|---|---|---|
| 3 | 1250000 | TTTTTCCGG | TTTTTCCGG | TTTTTCCGG | TTTTTCCGG |
| 3 | 1750000 | ACGCCTGAC | ACGCCTGAC | ACGCCTGAC | ACGCCTGAC |
| 3 | 2250000 | CGTGGCGAT | AGTGGCGAT | CGTGGCGAT | CGTGGCGAT |
| 3 | 2520748 | TAATTCCAC | TAATGCCAC | TAATkCCAC | TAATkCCAC |
| 4 | 100004 | GAGTAATGA | GAGTGATAA | GAGTrATrA | GAGTrATrA |
| 4 | 340893 | AGGAGGTAC | AGGTGGTAT | AGGrGGTAy | AGGrGGTAy |
| 4 | 598147 | GATCAACAG | GATCGACAG | GATCrACAG | GATCrACAG |
| 4 | 852119 | CGAACACTC | CGAATATTC | CGAAyAyTC | CGAAyAyTC |
| 4 | 1100085 | GATGACGAA | GATGCCGAA | GATGmCGAA | GATGmCGAA |
| 4 | 1350536 | CGAAACCGG | CGAACTCGG | CGAAmyCGG | CGAAmyCGG |
| 4 | 1599885 | GATAATTGC | GATACTTGC | GATAmTTGC | GATAmTTGC |
| 4 | 1850288 | ATTCACGTA | ATTCGTGTA | ATTCryGTA | ATTCryGTA |
| 4 | 2100356 | TCAGGGACC | TCAGAGACC | TCAGrGACC | TCAGrGACC |
| 4 | 2284257 | TCTGAACTG | TCTGGACTG | TCTGrACTG | TCTGrACTG |
| 5 | 100211 | TCCTCGAAT | TCCTTGAAT | TCCTyGAAT | TCCTyGAAT |
| 5 | 350872 | GGCGCGCCC | GGCGTGCCC | GGCGyGCCC | GGCGyGCCC |
| 5 | 599922 | CGTCGTTCA | CGTCATTCA | CGTCrTTCA | CGTCrTTCA |
| 5 | 851262 | TAATCGTCT | TAATTCTCT | TAATysTCT | TAATysTCT |
| 5 | 1099776 | ACATCGACA | ACATTGACA | ACATyGACA | ACATyGACA |
| 5 | 1352539 | TTGTTGTCC | TTGTGATCC | TTGTkrTCC | TTGTkrTCC |
| 5 | 1599904 | AACTCCCTT | AACTTCCTT | AACTyCCTT | AACTyCCTT |
| 5 | 1851458 | AAATTCTCC | AAATAATCC | AAATwmTCC | AAATwmTCC |
| 5 | 2100025 | CCCTCAGTC | CCCTTAGTC | CCCTyAGTC | CCCTyAGTC |
| 5 | 2278878 | GGTCAAAAA | GGTCGAAAA | GGTCrAAAA | GGTCrAAAA |
| 6 | 106294 | GCCACCTGA | GCCATCTCG | GCCAyCTCr | GCCAyCTCr |
| 6 | 350337 | CATTCGGTT | CATTTGGTT | CATTyGGTT | CATTyGGTT |
| 6 | 600047 | GGAGTATTT | GGAGCATTT | GGAGyATTT | GGAGyATTT |
| 6 | 849990 | AGTTTAGGA | AGTTCAGGA | AGTTyAGGA | AGTTyAGGA |
| 6 | 1098535 | CAAAAATTG | CAAAGATTG | CAAArATTG | CAAArATTG |
| 6 | 1349453 | TGTCAATAG | TGTCGGTAG | TGTCrrTAG | TGTCrrTAG |
| 6 | 1600000 | AAACCTGGA | AAACCTGGA | AAACCTGGA | AAACCTGGA |
| 6 | 1676645 | AACCAGATT | AACCGGATT | AACCrGATT | AACCrGATT |
| 6 | 2000087 | GATTCTGCG | GATTTTGCG | GATTyTGCG | GATTyTGCG |
| 6 | 2252662 | GGGTCGGTA | GGGTTGGTA | GGGTyGGTA | GGGTyGGTA |
| 7 | 100284 | GAAACTCAG | GAAATTCAG | GAAAyTCAG | GAAAyTCAG |
| 7 | 350044 | ATATCCTTT | ATATTCTTT | ATATyCTTT | ATATyCTTT |
| 7 | 600111 | CAATCATTA | CAATTATTA | CAATyATTA | CAATyATTA |
| 7 | 850516 | TGACACATA | TGACGCATA | TGACrCATA | TGACrCATA |

TABLE VII-continued

| Position of SNA | | Culture: | | | |
|---|---|---|---|---|---|
| Scaffold | [H97 V2.0 ref. coords.] | J10102-s69 | OWNC | J11500 | J11500-ms2 |
| 7 | 1100248 | TCAC*A*GAAG | TCACGGAAG | TCAC*r*GAAG | TCAC*r*GAAG |
| 7 | 1350089 | CTTT*C*CCCC | CTTTTCCCC | CTTT*y*CCCC | CTTT*y*CCCC |
| 7 | 1605047 | ATAC*G*TG*A*C | ATACTTGGC | ATAC*k*TG*r*C | CTAC*k*TG*r*C |
| 7 | 1850000 | GAGA*T*ACT | GAGA*T*ACT | GAGA*T*ACT | GAGA*T*ACT |
| 7 | 1898793 | TCCG*T*AT*G*A | TCCGCATAA | TCCG*y*AT*r*A | TCCG*y*AT*r*A |
| 7 | 1991505 | TCTA*AA*GTT | TCTACGGTT | TCTA*mr*GTT | TCTA*mr*GTT |
| 8 | 350000 | ATTG*A*CGCG | ATTG*A*CGCG | ATTG*A*CGCG | ATTG*A*CGCG |
| 8 | 600000 | CATT*G*ACGG | CATT*G*ACGG | CATT*G*ACGG | CATT*G*ACGG |
| 8 | 1100000 | CATA*C*GATC | CATA*C*GATC | CATA*C*GATC | CATA*C*GATC |
| 8 | 1350000 | AGCT*T*AACA | AGCT*T*AACA | AGCT*T*AACA | AGCT*T*AACA |
| 8 | 1600100 | CTGA*A*CCCT | CTGA*A*CCCT | CTGA*A*CCCT | CTGA*A*CCCT |
| 9 | 100105 | CTCA*G*CCGA | CTCAACCGA | CTCA*r*CCGA | CTCA*r*CCGA |
| 9 | 352455 | AGTC*T*CCA | AGTCCTCCA | AGTC*yy*CCA | AGTC*yy*CCA |
| 9 | 599950 | TGGT*G*TCCC | TGGTATCCC | TGGT*r*TCCC | TGGT*r*TCCC |
| 9 | 1010845 | GGGT*A*GTGA | GGGTGGTGA | GGGT*r*GTGA | GGGT*r*GTGA |
| 9 | 1244202 | GATG*G*AGAT | GATGAAGAT | GATG*r*AGAT | GATG*r*AGAT |
| 9 | 1504476 | TACT*A*TACC | TACTGTACC | TACT*r*TACC | TACT*r*TACC |
| 9 | 1656962 | TATC*C*ACTG | TATCTACTG | TATC*y*ACTG | TATC*y*ACTG |
| 10 | 100438 | AATT*C*ATTT | AATTAATTT | AATT*m*ATTT | AATT*m*ATTT |
| 10 | 350030 | GCGG*T*TCAA | GCGGCTCAA | GCGG*y*TCAA | GCGG*y*TCAA |
| 10 | 600032 | TTAC*G*CTGG | TTACACTGG | TTAC*r*CTGG | TTAC*r*CTGG |
| 10 | 850000 | TCGG*T*CGGA | TCGG*T*CGGA | TCGG*T*CGGA | TCGG*T*CGGA |
| 10 | 860249 | CCGC*G*AAATT | CCGCAAATT | CCGC*r*AAATT | CCGC*r*AAATT |
| 10 | 1109960 | AGGA*A*ATGA | AGGAAATGA | AGGA*r*ATGA | AGGA*r*ATGA |
| 10 | 1303902 | TGAT*C*TACT | TGATTTACT | TGAT*y*TACT | TGAT*y*TACT |
| 10 | 1490452 | AATC*T*GATG | AATCAGATG | AATC*w*GATG | AATC*w*GATG |
| 11 | 100000 | TATT*C*TTAG | TATT*C*TTAG | TATT*C*TTAG | TATT*C*TTAG |
| 11 | 350000 | GTCA*G*CAAG | GTCA*G*CAAG | GTCA*G*CAAG | GTCA*G*CAAG |
| 11 | 600000 | ATGG*G*CGCG | ATGG*G*CGCG | ATGG*G*CGCG | ATGG*G*CGCG |
| 11 | 850000 | CTTC*C*CCAT | CTTC*C*CCAT | CTTC*C*CCAT | CTTC*C*CCAT |
| 11 | 1100000 | TTAC*A*GTTG | TTAC*A*GTTG | TTAC*A*GTTG | TTAC*A*GTTG |
| 11 | 124000 | AGCC*A*AGTA | AGCC*A*AGTA | AGCC*A*AGTA | AGCC*A*AGTA |
| 12 | 100000 | CCTT*C*TAGT | CCTT*C*TAGT | CCTT*C*TAGT | CCTT*C*TAGT |
| 12 | 1000000 | CGAG*G*AGGA | CGAG*G*AGGA | CGAG*G*AGGA | CGAG*G*AGGA |
| 13 | 100697 | ACGT*A*TTTA | ACGTCTTTA | ACGT*m*TTTA | ACGT*m*TTTA |
| 13 | 370521 | TTTG*T*GTCA | TTTGAGTCA | TTTG*w*GTCA | TTTG*w*GTCA |
| 13 | 604345 | CTTC*C*GCAT | CTTCAGCAT | CTTC*m*GCAT | CTTC*m*GCAT |
| 13 | 850249 | GG*T*TG*GT*A | GGCTAGTAA | GG*y*T*r*GT*r*A | GG*y*T*r*GT*r*A |

TABLE VII-continued

| Scaffold | Position of SNA [H97 V2.0 ref. coords.] | Culture: J10102-s69 | OWNC | J11500 | J11500-ms2 |
|---|---|---|---|---|---|
| 14 | 113109 | AGGG***G***AATA | AGGGAAATA | AGGG***r***AATA | AGGG***r***AATA |
| 14 | 372086 | CGAT***T***C***T***TT | CGATCCCTT | CGAT***y***C***y***TT | CGAT***y***C***y***TT |
| 14 | 725684 | ATGA***A***TT***T***G | ATGAGTTCG | ATGA***r***TT***y***G | ATGA***r***TT***y***G |
| 15 | 150013 | GTGG***A***CCGT | GTGGCCCGT | GTGG***m***CCGT | GTGG***m***CCGT |
| 15 | 449866 | GAAT***C***TCGG | GAATTTCGG | GAAT***y***TCGG | GAAT***y***TCGG |
| 16 | 208609 | CACA***C***GCAC | CACATGCAC | CACA***y***GCAC | CACA***y***GCAC |
| 16 | 400000 | CCTC***G***GATT | CCTC***G***GATT | CCTC***G***GATT | CCTC***G***GATT |
| 17 | 120000 | TATT***C***TTCA | TATT***C***TTCA | TATT***C***TTCA | TATT***C***TTCA |
| 17 | 338415 | TGAG***G***AGCC | TGAGAAGCC | TGAG***r***AGCC | TGAG***r***AGCC |
| 17 | 449833 | ATCA***A***AC***T***A | ATCAGACAA | ATCA***r***AC***w***A | ATCA***r***AC***w***A |
| 18 | 101884 | ATTA***T***GGAC | ATTACGGAC | ATTA***y***GGAC | ATTA***y***GGAC |
| 19 | 98377 | GCTA***C***TGGG | GCTATTGGG | GCTA***C***TGGG | GCTA***C***TGGG |

Table VII presents a 'fingerprint' excerpted from the SNP (Single Nucleotide Polymorphism) marker genotype of the entire genome sequences of line J10102-s69, of line OWNC, of the F1 hybrid J11500 strain obtained from the mating of lines J10102-s69 and OWNC, and of the J11500-ms2 EDV of strain J11500. The IUPAC nucleotide and ambiguity codes are used to represent the observed 9-base DNA marker sequences reported above, each of which represents a genotypic marker locus. The identity of each marker locus is specified by the scaffold and SNP position information derived from the H97 V2.0 reference genome sequence published by the U.S. Department of Energy Joint Genome Institute (Morin et al. 2012). It is evident that a composite relationship of the heteroallelic genotype of strain J11500 exists with respect to the homoallelic genotypes of its two parental lines, namely line J10102-s69 and line OWNC. It is further evident that the heterokaryon genotype of the example EDV J11500-ms2 matches that of its initial strain, J11500.

A brief description of the genotype of strain J11500 at further six unlinked marker loci is provided below. Because the J11500 heterokaryon incorporates two sets of chromosomes, there are two allelic copies (two characters or elements of the genotype) at each marker locus. The brief genotype excerpt provided below therefore consists of 12 characters or elements. The brief genotype was prepared by the assignee of record using targeted Polymerase Chain Reactions to amplify genomic regions bracketing the defined markers from each of the culture DNAs. Any suitable PCR primers that bracket the defined marker regions may be used for this purpose; methods of designing suitable primers are well known in the art. The amplified PCR product DNA was sequenced by a contractor, Eurofins, using methods of their choice, and the genotypes were determined by direct inspection of these sequences in comparison to Sylvan America's database of reference marker/allele sequences.

Description of the p1n150-G3-2 Marker:

The 5' end of this marker segment begins at position 1 with the first "<u>T</u>" in the sequence <u>T</u>CCCAAGT, corresponding to H97 JGI V2.0 Scaffold 1 position 868615 (Morin et al. 2012) and extending in a reverse orientation (relative to the scaffold orientation) for ca. 600 nt in most alleles; an insertion in the DNA of allele 1T has produced a longer segment. At present, 9 alleles incorporating at least 30 polymorphic positions have been documented from diverse strains in Sylvan America's breeding collection.

Alleles present in the J10102-s69 and J11500 pedigree over three generations are alleles 1T, 2, 3, 4, and 9, characterized as follows (using the format: nucleotide base character @ alignment position, based on alignment of alleles 2, 3, and 4, and the alignable portions of allele 1T):

Allele 1T: 'C' @ 193; insertion of Abr1 transposon of 320 nt @ 206^207; 'T' @ 327; 'C' @ 374; 'G' @ 378; 'G' @ 422; 'C' @ 431; 'G' @ 472; etc.

Allele 2: no Abr1 insertion; 'C' @ 193; 'C' @ 327, 'C' @ 374; 'C' @ 378; 'G' @ 422; 'T' @ 431; 'G' @ 472; etc.

Allele 3: no Abr1 insertion; 'C' @ 193; 'T' @ 327, 'G' @ 374; 'C' @ 378; 'G' @ 422; 'T' @ 431; 'A' @ 472; etc.

Allele 4: no Abr1 insertion; 'C' @ 193; 'T' @ 327, 'C' @ 374; 'C' @ 378; 'A' @ 422; 'T' @ 431; 'G' @ 472; etc.

Allele 9: no Abr1 insertion; 'G' @ 193; 'C' @ 327, 'C' @ 374; 'C' @ 378; 'G' @ 422; 'T' @ 431; 'G' @ 472; etc.

Because of linkage to the MAT locus, which is obligately heteroallelic in fertile heterokaryons, genotypes of all known and expected heterokaryons at p1n150-G3-2 are also heteroallelic.

The J10102 heterokaryon has an '1/2' heteroallelic genotype.

The U1 heterokaryon has an '1/2' heteroallelic genotype.

'Off-White' heterokaryons such as Somycel 76 have a '1/3' heteroallelic genotype.

'Smooth-White' heterokaryons such as Somycel 53 have a '2/3' heteroallelic genotype.

The J9277 heterokaryon has a '1/4' heteroallelic genotype.

The genotype of the J11500 heterokaryon at the p1n150-G3-2 marker 'locus' is '1/2' (heteroallelic), designating the presence of alleles 1 and 2. Allele 1 was contributed by the OWNC line. Allele 2 was transmitted from the J10102 heterokaryon via the J10102-s69 homokaryon. The '1/2' genotype distinguishes J11500 from many other heterokaryons including from all of its own grandparents, although not from the U1 strain family.

Description of the ITS (=ITS 1+2 Region) Marker:

The ITS segment is part of the nuclear rDNA region, which is a cassette that is tandemly repeated up to an estimated 100 times in the haploid genome of *A. bisporus*. Therefore there is no single precise placement of this sequence in the assembled H97 genome, and in fact it is difficult or impossible to precisely assemble the sequence over all of the tandem repeats. Three cassette copies were included on scaffold 10 of the H97 JGI V2.0 assembly, beginning at position 1612110; a partial copy is also assembled into scaffold 29 (Morin et al. 2012). The 5' end of this marker segment begins at position 1 with the first "G" in the sequence GGAAGGAT, and extending in a forward orientation (relative to the scaffold orientation) for ca. 703-704 nt in most alleles. At present, more than 9 alleles incorporating at least 11 polymorphic positions have been documented from diverse strains in Sylvan's breeding collection.

Alleles present in the J10102-s69 and J11500 immediate pedigree are alleles I1, I2, and I4, characterized as follows (using the format: nucleotide base character @ alignment position, based on alignment of 9 alleles).

Allele I1: 'C' @ 52; 'T' @ 461; 'T' @ 522; 'T' @ 563; etc.

Allele I2: 'T' @ 52; 'T' @ 461; 'T' @ 522; 'T' @ 563; etc.

Allele I4: 'C' @ 52; 'A' @ 461; 'C' @ 522; 'C' @ 563; etc.

The J10102 heterokaryon has an 'I1/I4' heteroallelic genotype.

The U1 heterokaryon has an 'I1/I2' heteroallelic genotype.

The genotype of the J11500 heterokaryon at the ITS marker 'locus' is 'I1/I4' (heteroallelic), designating the presence of alleles I1 and I4. Allele I1 was contributed by the OWNC line. Allele I4 was transmitted from the J10102 heterokaryon via the J10102-s69 homokaryon. This distinguishes J11500 from the U1 strain family, which has an 'I1/I2' genotype.

Description of the MFPC-1-ELF Marker:

The 5' end of this marker segment begins at position 1 with the first "G" in the sequence GGGAGGGT, corresponding to H97 JGI V2.0 Scaffold 8 position 829770 (Morin et al. 2012) and extending in a forward orientation (relative to the scaffold orientation) for ca. 860 nt in most alleles. At present, at least 7 alleles incorporating at least 40 polymorphic positions have been documented from diverse strains in Sylvan's breeding collection.

Alleles present in the J10102-s69 and J11500 immediate pedigree, are alleles E1, E2, and E8, characterized as follows (using the format: nucleotide base character @ alignment position, based on alignment of 8 alleles).

Allele E1: 'A' @ 77; 'A' @ 232; 'A' @ 309; 'T' @ 334; 'A' @ 390; 'A' @ 400; 'T' @ 446, 'A' @ 481; etc.

Allele E2: 'G' @ 77; 'A' @ 232; 'G' @ 309; 'T' @ 334; 'G' @ 390; 'G' @ 400; 'C' @ 446, 'G' @ 481; etc.

Allele E8: 'A' @ 77; 'G' @ 232; 'G' @ 309; 'A' @ 334; 'A' @ 390; 'A' @ 400; 'C' @ 446, 'G' @ 481; etc.

The J10102 heterokaryon has an 'E1/E8' heteroallelic genotype.

The U1 heterokaryon has an 'E1/E2' heteroallelic genotype.

The genotype of the J11500 heterokaryon at the MFPC-1-ELF marker 'locus' is 'E1/E1', designating the presence of two copies of alleles E1. One copy of allele E1 was contributed by the OWNC line; a second copy of allele E1 was transmitted from the J10102 heterokaryon via the J10102-s69 homokaryon. This homoallelic genotype distinguishes J11500 from the predominant U1-type of commercial cultivar, which has an 'E1/E2' genotype.

Description of the AN marker:

The 5' end of this marker segment begins at position 1 with the first "G" in the sequence GGGTTTGT, corresponding to H97 JGI V2.0 Scaffold 9 position 1701712 (Morin et al. 2012) and extending in a forward orientation (relative to the scaffold orientation) for ca. 1660 nt (in the H97 genome) to 1700 nt (in the alignment space) in known alleles; several insertions/deletions have created length polymorphisms which, in addition to point mutations of individual nucleotides, characterize the alleles. At present, 5 alleles incorporating more than 70 polymorphic positions have been documented from diverse strains in Sylvan's breeding collection.

Alleles present in the J10102-s69 and J11500 immediate pedigree are alleles N1, N2 and N5, characterized in part as follows (using the format: nucleotide base character @ alignment position, based on alignment of alleles N1 through N5):

Allele N1: 'G' @ 640; [deletion] @ 844-846; 'T' @ 882; 'A' @ 994, etc.

Allele N2: 'A' @ 640; [deletion] @ 844-846; 'T' @ 882; 'A' @ 994, etc.

Allele N5: 'A' @ 640; 'ACG' @ 844-846; 'C' @ 882; 'G' @ 994, etc.

The J10102 heterokaryon has an 'N1/N5' heteroallelic genotype.

The U1 heterokaryon has an 'N1/N2' heteroallelic genotype.

The genotype of the J11500 heterokaryon at the AN marker 'locus' is 'N1/N5' (heteroallelic), designating the presence of alleles N1 and N5. Allele N1 was contributed by the OWNC line. Allele N5 was transmitted from the J10102 heterokaryon via the J10102-s69 homokaryon.

The 'N1/N5' genotype at the AN marker locus distinguishes J11500 from commercial strains U1 and A-15, which have an 'N1/N2' genotype. This element of the genotype fingerprint can also distinguish J11500 from among many other strains.

Description of the AS Marker:

The 5' end of this marker segment begins at position 1 with the first "G" in the sequence GG(T/N)GTGAT, corresponding to H97 JGI V2.0 Scaffold 4 position 752867 (Morin et al. 2012) and extending in a forward orientation (relative to the scaffold orientation) for ca. 1620 nt (in the H97 genome) to 1693 nt (in the alignment space) in known alleles; several insertions/deletions have created length polymorphisms which, in addition to point mutations of individual nucleotides, characterize the alleles. At present, 7 alleles incorporating more than 80 polymorphic positions have been documented from diverse strains in Sylvan's breeding collection.

Alleles present in the J10102-s69 and J11500 immediate pedigree are alleles SC and SD, characterized in part as follows (using the format: nucleotide base character @ alignment position, based on alignment of alleles SA through SG):

Allele SC: 'T' @ 28; 'GATATC' @ 258-263; 'G' @ 275; [insertion]+VTTTCTCAGC'+[insertion] @ 309-349; 'C' @ 404, etc.

Allele SD: 'C' @ 28; [deletion] @ 258-263; 'T' @ 275; [deletion] @ 309-349; 'T' @ 404, etc.

The J10102 heterokaryon has an 'SC/SD' heteroallelic genotype.

The U1 heterokaryon has an 'SC/SD' heteroallelic genotype.

The genotype of the J11500 heterokaryon at the AS marker 'locus' is 'SC/SD' (heteroallelic), designating the presence of alleles SC and SD. Allele SD was contributed by the OWNC line. Allele SC was transmitted from the J10102 heterokaryon via the J10102-s69 homokaryon.

The 'SC/SD' genotype at the AS marker locus is also shared by commercial strains U1 and A-15. While this element of the genotype fingerprint distinguished J11500 from among many other strains, it does not distinguish J11500 from the U1 strain family.

Description of the FF Marker:

The 5' end of this marker segment begins at position 1 with the first "T" in the sequence TTCGGGTG, corresponding to H97 JGI V2.0 Scaffold 12 position 281674 (Morin et al. 2012) and extending in a forward orientation (relative to the scaffold orientation) for ca. 570 nt in most alleles. At present, 7 alleles incorporating at least 20 polymorphic positions have been documented from diverse strains in Sylvan's breeding collection.

Alleles present in the J10102-s69 and J11500 immediate pedigree are Alleles FF1 and FF2, characterized as follows (using the format: nucleotide base character @ alignment position, based on alignment of alleles 1 and 2):

Allele FF1: 'CCG' @ 48-50

Allele FF2: 'TTC' @ 48-50

The J10102 heterokaryon has an 'FF1/FF2' heteroallelic genotype.

The U1 heterokaryon has an 'FF1/FF2' heteroallelic genotype.

The genotype of the J11500 heterokaryon at the FF marker 'locus' is 'FF1/FF1' (homoallelic), designating the presence of two copies of allele FF-1, contributed by both the OWNC line and the J10102-s69 homokaryon. This distinguishes J11500 from the predominant U1-type of commercial cultivar, which has an 'FF1/FF2' genotype. This element of the genotype fingerprint can also distinguish J11500 from among many other strains.

A deposit of a culture of an example of an EDV, namely strain J11500-ms2, obtained from hybrid strain J11500, as disclosed herein, has also been made with the Agricultural Research Services Culture Collection (NRRL) 1815 North University Street, Peoria, Ill. 61604 USA. The date of deposit was Jan. 15, 2014. The culture deposited was taken from the same culture maintained by Sylvan America, Inc., Kittanning, Pa., the assignee of record, since prior to the filing date of this application. All restrictions upon the deposit have been removed, and the deposit is intended to meet all deposit requirements of the U.S. Patent and Trademark Office, including 37 C.F.R. Sec. 1.801-1.809, and all deposit requirements under the Budapest Treaty. The NRRL Accession No. is 50896. The deposit will be maintained in the depository for a period of 30 years, or 5 years after the last request, or for the effective life of the patent, whichever is longer, and will be replaced as necessary during that period. The culture will be irrevocably and without restriction or condition released to the public upon filing of a priority application or upon the issuance of a patent according to the patent laws.

Further, the two parent lines of J11500 have also been deposited. Specifically, a deposit of a culture of the *Agaricus bisporus* homokaryotic line J10102-s69, as disclosed herein, has been made with the Agricultural Research Services Culture Collection (NRRL) 1815 North University Street, Peoria, Ill. 61604 USA. The date of deposit was Jan. 15, 2014. The culture deposited was taken from the same culture maintained by Sylvan America, Inc., Kittanning, Pa., the assignee of record, since prior to the filing date of this application. All restrictions upon the deposit have been removed, and the deposit is intended to meet all deposit requirements of the U.S. Patent and Trademark Office, including 37 C.F.R. Sec. 1.801-1.809, and all deposit requirements under the Budapest Treaty. The NRRL Accession No. is 50893. The deposit will be maintained in the depository for a period of 30 years, or 5 years after the last request, or for the effective life of the patent, whichever is longer, and will be replaced as necessary during that period. The culture will be irrevocably and without restriction or condition released to the public upon filing of a priority application or upon the issuance of a patent according to the patent laws.

In addition, a deposit of a culture of the *Agaricus bisporus* homokaryotic line OWNC, as disclosed herein, has been made with the Agricultural Research Services Culture Collection (NRRL) 1815 North University Street, Peoria, Ill. 61604 USA. The date of deposit was Jan. 15, 2014. The culture deposited was taken from the same culture maintained by Sylvan America, Inc., Kittanning, Pa., the assignee of record, since prior to the filing date of this application. All restrictions upon the deposit have been removed, and the deposit is intended to meet all deposit requirements of the U.S. Patent and Trademark Office, including 37 C.F.R. Sec. 1.801-1.809, and all deposit requirements under the Budapest Treaty. The NRRL Accession No. is 50894. The deposit will be maintained in the depository for a period of 30 years, or 5 years after the last request, or for the effective life of the patent, whichever is longer, and will be replaced as necessary during that period. The culture will be irrevocably and without restriction or condition released to the public upon filing of a priority application or upon the issuance of a patent according to the patent laws.

One use of the culture of strain J11500 is the production of crops of edible mushrooms for sale. Another use is for the improvement of facility hygiene via strain rotation and a 'virus-breaking' effect. A third use is to incorporate the genetic material of strain J11500 into offspring and derived or descended cultures including dormant and germinating spores and protoplasts. Additional uses also exist as noted above.

Hybridization of *Agaricus bisporus* cultures of the invention may be accomplished by allowing two different cultures, one of which is a genetic line present in a spore of J11500, to grow together in close proximity, preferably on sterile media, until anastomosis (i.e., hyphal or cell fusion) occurs. In a successful mating, the resultant fusion culture is a first-generation outbred hybrid culture incorporating a genetic line present in a mushroom spore which is one part of one embodiment of the present invention. Protoplasts derived from basidia or other parts of the organism are another part of the J11500 mushroom that may be used to transmit genetic material of J11500 into new cultures.

Methods for obtaining, manipulating, and mating cultures of the present invention, for producing offspring, inoculum, products, and crops of the current invention, for using a strain rotation program to improve mushroom farm hygiene, and for obtaining the genotypic fingerprint of mushroom cultures, are described hereinabove and are also well known to practitioners of the art.

In order to demonstrate practice of the invention, a subculture of strain J11500 was propagated as described above to produce spawn and casing inocula, which were used to produce crops of white mushrooms under standard commercial cultivation practices as described herein above (see Background of Invention section). Commercial culture inocula including mushroom 'spawn' and 'casing inoculum' were prepared using commercial large-scale microbiological production methods, namely, by aseptically introducing inoculum of a pure culture of strain J11500 into from one to about 2,000 liters of sterilized growth media under sterile conditions, and were disbursed into sterile packaging for test purposes. The mushroom spawn was mixed with pasteurized compost and incubated for 13 to 18 days. A non-nutritive peat-based casing layer was placed over the compost as previously described and a casing inoculum was incorporated into the casing layer. Under controlled environmental conditions, the first mushrooms reached the correct stage of development in a further 14 days. The mushrooms were picked over a 3 to 4 day period. Three flushes of mushrooms were harvested before each test was concluded.

The mushrooms produced by strain J11500 have a white pileus color. As the Royal Horticultural Society (RHS) color charts do not provide a reference standard for the color "white", direct measurements of color of the strain J11500 mushroom cap have been made using a Minolta Chromameter and the L-a-b color space system. One measurement was made on the caps of each of ten first break mushrooms grown in a testing facility. The mean values, plus or minus the standard error, for the measured L, a, and b color components were as follows: $L=89.58\pm0.11$; $a=-1.21\pm0.015$; $b=8.12\pm0.088$. Colors within or substantially coinciding with color space described by these three parameter distributions are called "white" according to standard and accepted practices of the commercial mushroom industry.

Strain J10102 is a heterokaryotic strain obtained in Sylvan America, Inc.'s strain development program. It did not have the combination of characters needed to be successful commercially; however its performance and physical characteristics approached those criteria, and the strain was assessed as having some unknown potential for further development and improvement. Consequently, J10102 was used as a parent in 165 matings to several diverse lines of *A. bisporus* that, it was believed, might have had some useful potential in mating combinations. Individual outcomes were unpredictable and variable; it was hoped that the experiment might produce a successful result but the overall likelihood of that was considered to be low. Of the 165 novel hybrids obtained, only two were of potential commercial interest, and only one, J11500, consistently met the target criteria for a successful commercial strain. It was later determined in the course of testing that strain J11500 had other beneficial attributes as well.

Essentially Derived Varieties of strain J11500 were obtained from single spores, multiple spore mixtures, and from tissue and somatic selections, as described hereinabove. Spores of strain J11500 were obtained and were germinated and used to produce heterokaryotic and homokaryotic offspring as described hereinabove. Homokaryotic offspring lines were used to make matings to other lines, and further hybrids were obtained from these matings. Spawn and casing inoculum of J11500 and A-15 were used in self/self and self/non-self combinations in test crops to confirm the incompatibility of the two strains, a prerequisite for use in virus-breaking strategies, all as described hereinabove.

Although the invention has been described in terms of particular embodiments in this application, one of ordinary skill in the art, in light of the teachings herein, can generate additional embodiments and modifications without departing from the spirit of, or exceeding the scope of, the claimed invention. Accordingly, it is understood that the descriptions herein are proffered only to facilitate comprehension of the invention and should not be construed to limit the scope thereof.

What is claimed is:

1. A hybrid mushroom culture of *Agaricus bisporus* designated as strain J11500, a representative culture of the strain having been deposited under NRRL Accession No. 50895.

2. A part of the hybrid mushroom culture of claim 1 selected from the group consisting of hyphae, spores, cells, nuclei, and protoplasts.

3. The part of the hybrid mushroom culture of claim 2, wherein the spores are selected from dormant and germinated spores, and wherein the dormant and germinated spores include heterokaryons and homokaryons incorporated therein.

4. A product comprising the hybrid mushroom culture of *Agaricus bisporus* designated as strain J11500 of claim 1, the product selected from the group consisting of mycelium, spawn, inoculum, casing inoculum, fresh mushrooms, processed mushrooms, mushroom pieces, and colonized substrates including grain, compost, and friable particulate matter.

5. An Essentially Derived Variety of the hybrid mushroom culture of claim 1, wherein said Essentially Derived Variety is a culture of a strain derived from a single initial culture of strain J11500, wherein a culture of the strain has been deposited under NRRL Accession No. 50895, such that at least 75% of its genome or genotype is present in the genome or genotype of the initial culture of strain J11500.

6. A hybrid mushroom culture of *Agaricus bisporus* having a genotypic fingerprint which has alleles at marker loci ITS, p1n150-G3-2, MFPC-1-ELF, AN, AS, and FF, wherein all of the alleles at marker loci ITS, p1n150-G3-2, MFPC-1-ELF, AN, AS, and FF of said fingerprint are present in the genotypic fingerprint of strain J11500, wherein a culture of strain J11500 has been deposited under NRRL Accession No. 50895.

7. The hybrid mushroom culture of claim 6, wherein said culture has a genotypic fingerprint which has characters at marker loci described in Table VII, wherein all of the characters of said fingerprint are present in the genotypic fingerprint of strain J11500, wherein a culture of strain J11500 has been deposited under NRRL Accession No. 50895.

8. An *Agaricus bisporus* culture having all of the physiological and morphological characteristics of strain J11500, wherein a culture of strain J11500 has been deposited under the NRRL Accession Number 50895.

9. A method of producing a hybrid mushroom culture of *Agaricus bisporus* comprising: mating a homokaryotic line J10102-s69, a culture of which has been deposited under NRRL Accession No. 50893, with a homokaryotic line OWNC, a culture of which has deposited under NRRL Accession No. 50894.

10. The method of claim 9, wherein said hybrid mushroom culture exhibits antagonism toward heterokaryon strains in the U1 derived lineage group.

11. The method according to claim 9, further comprising: providing the mushroom culture in mushroom products selected from the group consisting of mycelium, spawn, inoculum, casing inoculum, fresh mushrooms, processed mushrooms, parts of mushrooms, mushroom pieces, and colonized substrates including grain, compost, and friable particulate matter.

12. The method according to claim 9, further comprising: providing the mushroom culture in derived cultures selected from the group consisting of homokaryons, heterokaryons, aneuploids, somatic subcultures, tissue explants cultures, protoplasts, dormant spores, germinating spores, inbred descendents and outbred descendents, transgenic cultures, and cultures having a genome incorporating a single locus conversion.

13. A culture produced by the method of claim 9.

14. The method of claim 10, further comprising growing the hybrid mushroom culture to produce hybrid mushrooms and parts of mushrooms.

15. The method of claim 9, wherein the hybrid mushroom culture produced comprises a marker profile having alleles at marker loci ITS, p1n150-G3-2, MFPC-1-ELF, AN, AS, and FF, wherein all of the alleles at marker loci ITS, p1n150-G3-2 MFPC-1-ELF, AN, AS, and FF of said marker profile are also present in the marker profile of J11500.

16. A cell of the hybrid culture produced by the method of claim 9.

17. The cell of claim 16, further comprising a marker profile having alleles at marker loci ITS, p1n150-G3-2, MFPC-1-ELF, AN, AS, and FF, wherein all of the alleles at marker loci ITS, p1n150-G3-2 MFPC-1-ELF, AN, AS, and FF of said marker profile are also present in the marker profile of J11500.

18. The cell of claim 17, further comprising a marker profile having characters at marker loci described in Table VII, wherein all of the characters of said marker profile are also present in the marker profile of J11500.

19. A culture comprising the cell of claim 16.

20. A method comprising using a hybrid mushroom culture selected from strain J11500 or Essentially Derived Varieties of strain J11500, wherein said Essentially Derived Varieties are cultures of a strain derived from a single initial culture of strain J11500, such that at least 75% of its genome or genotype is present in the genome or genotype of the initial culture of strain J11500, a representative culture of the strain J11500 having been deposited under NRRL Accession No. 50895.

21. The method of claim 20, further comprising: growing a crop of edible mushrooms.

22. The method of claim 20, further comprising: using strain J11500 or Essentially Derived Varieties of strain J11500 in crop rotation to reduce pathogen pressure and pathogen reservoirs in mushroom growing facilities.

23. The method of claim 20, further comprising using strain J11500 and Essentially Derived Varieties of strain J11500 to produce offspring.

* * * * *